(12) United States Patent
Pascal

(10) Patent No.: US 9,918,476 B2
(45) Date of Patent: Mar. 20, 2018

(54) METHOD FOR MANUFACTURING A PARASITICIDAL COMPOSITION

(71) Applicant: SOLVAY SA, Brussels (BE)

(72) Inventor: Jean-Philippe Pascal, Villers les Nancy (FR)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 14/366,083

(22) PCT Filed: Dec. 19, 2012

(86) PCT No.: PCT/EP2012/076125
§ 371 (c)(1),
(2) Date: Jun. 17, 2014

(87) PCT Pub. No.: WO2013/092694
PCT Pub. Date: Jun. 27, 2013

(65) Prior Publication Data
US 2014/0348892 A1    Nov. 27, 2014

(30) Foreign Application Priority Data

Dec. 19, 2011 (FR) .................................... 11 61937

(51) Int. Cl.
| | |
|---|---|
| *A01N 59/00* | (2006.01) |
| *A01N 25/08* | (2006.01) |
| *A01N 25/04* | (2006.01) |
| *A01N 25/12* | (2006.01) |
| *A01N 59/04* | (2006.01) |

(52) U.S. Cl.
CPC ............. *A01N 59/00* (2013.01); *A01N 25/04* (2013.01); *A01N 25/08* (2013.01); *A01N 25/12* (2013.01); *A01N 59/04* (2013.01)

(58) Field of Classification Search
CPC ........ A01N 25/04; A01N 59/00; A01N 59/04; A01N 25/12; A01N 25/08; A01N 2300/00
See application file for complete search history.

(56) References Cited

U.S. PATENT DOCUMENTS 5,468,715 A * 11/1995 Joseph ................... A01N 59/04
424/600
6,478,828 B1    11/2002 Ninane et al.
2006/0040031 A1   2/2006 Pascal et al.

FOREIGN PATENT DOCUMENTS

| EP | 0352847 A1 | 1/1990 |
|---|---|---|
| WO | WO 02/102158 A1 | 12/2002 |
| WO | WO 2004056184 A1 | 7/2004 |
| WO | WO 2005025317 A1 | 3/2005 |
| WO | WO 2006097480 A1 * | 9/2006 |
| WO | WO 2006097504 A1 | 9/2006 |
| WO | WO 2007045608 A1 | 4/2007 |
| WO | WO 2010121323 A1 * | 10/2010 |
| WO | WO 2012152952 A1 | 11/2012 |

OTHER PUBLICATIONS

U.S. Appl. No. 14/115,898, Philippe Lefevbre, et al, filed Nov. 6, 2013, WO 2012152952.
U.S. Appl. No. 10/539,570, Jean-Philippe Pascal, et al, filed Jun. 17, 2005, WO 2004056184.
U.S. Appl. No. 13/232,072, Jean-Philippe Pascal, et al, filed Sep. 14, 2011, WO 2004056184.
U.S. Appl. No. 10/571,930, Nicolas Palangie, et al, filed Mar. 15, 2006, WO 2005025317.
U.S. Appl. No. 11/908,683, Jean-Philippe Pascal, et al, filed Sep. 14, 2007, WO 2006097504.
U.S. Appl. No. 12/090,444, Nicolas Palangie, et al, filed Apr. 16, 2006, WO 2007045608.
U.S. Appl. No. 13/899,175, Nicolas Palangie, et al, filed May 21, 2013, WO 2007045608.

* cited by examiner

*Primary Examiner* — Anoop K Singh
*Assistant Examiner* — Doan T Phan
(74) *Attorney, Agent, or Firm* — Beatrice C. Ortego

(57) ABSTRACT

A method for manufacturing a parasiticidal composition comprising at least 40% of alkali metal bicarbonate and at least 1% of silica, wherein: at least 35% of the alkali metal bicarbonate of the composition is milled in the presence of silica in order to form a mixture of particles, and if necessary, the remainder of the alkali metal bicarbonate is added to the mixture of particles to form the parasiticidal composition, and wherein said parasiticidal composition has a particle size distribution such that at least 50% by weight of the particles have a diameter of less than 100 μm. A parasiticidal composition obtained by the present method and the use of the parasiticidal composition obtained by the present method in the form of a powder, a suspension or a gel.

18 Claims, No Drawings

METHOD FOR MANUFACTURING A PARASITICIDAL COMPOSITION

CROSS-REFERENCE TO RELATED APPLICATIONS

This application is a U.S. national stage entry under 35 U.S.C. § 371 of International Application No. PCT/EP2012/076125 filed Dec. 19, 2012, which claims the priority benefit to French application No. 11.61937 filed Dec. 19, 2011, the whole content of this application being incorporated herein by reference for all purposes.

TECHNICAL FIELD

The invention relates to a method for manufacturing a parasiticidal composition. It relates more particularly to a method for manufacturing a parasiticidal composition comprising alkali metal bicarbonate and silica, in which at least 35% of the alkali metal bicarbonate is milled in the presence of the silica and such that said parasiticidal composition consists of particles having a particle size distribution such that at least 50% by weight of the particles have a diameter of less than 100 μm.

The invention also relates to a parasiticidal composition capable of being obtained by this method and the use of the composition.

It also relates to the use of the parasiticidal composition in powder form or in the form of a suspension in a liquid.

The expression "parasiticidal composition" is understood to mean a composition in contact with which the parasites that have a tendency to develop in particular on cereal plants, or in the environment of livestock animals or pets or in the environment of humans, cannot survive.

The expression "parasites" is understood to mean arthropods such as insects, mites, fleas and ticks. The parasites may be in the egg, larval or adult stage.

The action of the composition may be direct. It may also be indirect, for example when the parasiticidal composition destroys a substance necessary to the survival of the parasite.

PRIOR ART

It is known practice to combat parasites by means of substances that are neurotoxic and growth inhibitors, such as for example: pyrethrinoids, organochlorinated compounds, organophosphorous compounds, and carbamates. These substances have the risk of also being toxic for humans or animals when their environments are treated with such substances. These products are applied either by spraying or by thermal fogging.

It is also known that the parasiticidal compositions based on natural or synthetic pyrethrinoids, or on organophosphorous compounds used as alternatives to organochlorinated compounds, have an effectiveness that decreases over time. These parasiticidal compositions have an action that could be described as "shock action". Their effectiveness is in general of the order of a few days, and at most of the order of a few weeks. This is due to non-zero vapour pressures of the components that give rise to their volatilization over time and moreover to their degradation by oxidation.

WO 2006/097480 describes a method for manufacturing a parasiticidal powder free of neurotoxic agents according to which two fine powders, one of sodium bicarbonate, the other of silica, are mixed in order to form a mixture of 85% by weight of sodium bicarbonate, for which 75% of the particles forming it have a diameter of less than 65 μm, and 15% of amorphous silica in a pedestal mixer for 10 minutes. The compositions have a good effectiveness on house mites, the mites and insects that develop in stocks of cereal plants, the mites that develop in the environment of livestock animals. These compositions may be used in powder form, for example on indoor rugs or carpets or incorporated into animal bedding or animal litter. They may also be used in the form of a suspension in a liquid, and applied by spraying.

Such formulations, which are not harmful for humans and animals, have the advantage of not degrading over time. They thus make it possible to combine a shock action with a preventive action in order to control the development of parasites over durations of more than 12 weeks.

It has surprisingly been observed that the mixing, by co-milling, of coarse particles of alkali metal bicarbonate in the presence of fine silica particles, made it possible to obtain a parasiticidal powder having a greatly increased effectiveness with respect to a composition containing the same proportion of bicarbonate and silica produced in the prior art by a first step comprising a fine milling of the alkali metal bicarbonate to the same particle size then, in a second step, by mixing with the fine silica.

The invention therefore aims to provide an improved method for manufacturing such parasiticidal mixtures, enabling an appreciable gain in the effectiveness of these mixtures both in terms of treatment action (shock treatment) and in terms of action over time for controlling the development of parasites (preventive treatment).

SUMMARY OF THE INVENTION

The invention relates to a method for manufacturing a parasiticidal composition comprising:
at least 40%, or at least 50%, or at least 60%, or at least 70%, or at least 80% by weight of alkali metal bicarbonate, and
at least 1%, advantageously at least 2%, more advantageously at least 5%, more advantageously still at least 10%, preferably at least 15%, more preferably at least 20% of silica,
characterized in that:
at least 35% of the alkali metal bicarbonate of the composition is milled in the presence of silica in order to form a mixture of particles, and
if necessary, the remainder of the alkali metal bicarbonate is added to the mixture of particles to form the parasiticidal composition, and
said parasiticidal composition has a particle size distribution such that at least 50% by weight of the particles have a diameter of less than 100 μm.

The invention also relates to the parasiticidal composition capable of being obtained by the present method and also to the use of the parasiticidal composition obtained by the present method in the form of a powder or a suspension.

DETAILED DESCRIPTION OF THE INVENTION

The invention relates to a method for manufacturing a parasiticidal composition comprising:
at least 40%, or at least 50%, or at least 60%, or at least 70%, or at least 80% by weight of alkali metal bicarbonate, and
at least 1%, advantageously at least 2%, more advantageously at least 5%, more advantageously still at least 10%, preferably at least 15%, more preferably at least 20% of silica, characterized in that:

at least 35% of the alkali metal bicarbonate of the composition is milled in the presence of silica in order to form a mixture of particles, and if necessary, the remainder of the alkali metal bicarbonate is added to the mixture of particles to form the parasiticidal composition, and said parasiticidal composition has a particle size distribution such that at least 50% by weight of the particles have a diameter of less than 100 µm.

Indeed, it has been observed that a co-milling of alkali metal bicarbonate in the presence of silica increases the synergy of the alkali metal bicarbonate with the silica and the effectiveness of the parasiticidal composition compared to the effectiveness of parasiticidal compositions obtained by milling the alkali metal bicarbonate then mixing the milled bicarbonate with the silica, even at equivalent final composition particle size. Only some of the alkali metal bicarbonate may be milled in the presence of silica. However, the more the percentage of the alkali metal bicarbonate co-milled in the presence of the silica is increased, the more the increase in the effectiveness against parasites increases. In the present invention it is recommended that at least 50%, advantageously at least 65%, preferably at least 80%, more preferably at least 90%, most preferably at least 95% of the alkali metal bicarbonate of the composition is milled in the presence of silica. In one particularly advantageous embodiment all of the alkali metal bicarbonate is milled in the presence of the silica.

In the present invention the alkali metal bicarbonate:silica weight ratio of the alkali metal bicarbonate milled in the presence of silica, is in general at most equal to: 100:1. It is advantageously at most 60:1, preferably at most 40:1, more preferably at most 20:1, most preferably at most 6:1.

The alkali metal bicarbonate:silica weight ratio of the alkali metal bicarbonate milled in the presence of silica, is in general at least equal to 1:4. It is advantageously at least 1:2, preferably at least 1:1, more preferably at least 2:1, most preferably at least 4:1.

The parasiticidal composition according to the present invention generally contains at most: 99%, or at most 95%, or at most 90%, or at most 85% by weight of sodium bicarbonate. It generally additionally comprises at most: 60%, or at most 50%, or at most 40%, or at most 30% by weight of silica.

The milling of the alkali metal bicarbonate in the presence of silica must be sufficient so that the mixture of particles thus obtained by milling has a particle size distribution such that at least 50% by weight of the particles have a diameter at most equal to: 70 µm, advantageously 50 µm, preferably 40 µm, more preferably 30 µm.

The weight-average diameter is measured by laser diffraction and scattering on a Malvern Mastersizer S particle size analyser using an He—Ne laser source having a wavelength of 632.8 nm and a diameter of 18 mm, a measurement cell equipped with a backscatter 300 mm lens (300 RF), an MS 17 liquid preparation unit, and an automatic solvent filtration kit ("ethanol kit") using ethanol saturated with bicarbonate.

In the variant according to the invention where only some of the alkali metal bicarbonate is co-milled with the silica, an additional amount of alkali metal bicarbonate may be added to the composition. In this variant, it is recommended that the parasiticidal composition has a particle size distribution such that at least 50% by weight of the particles which make it up have a diameter at most equal to: 100 µm, advantageously 70 µm, preferably 50 µm, more preferably 40 µm, most preferably 30 µm.

In the present invention, the alkali metal bicarbonate may, for example, be bicarbonate in the strict sense such as potassium bicarbonate or sodium bicarbonate. However, in this document it also covers compound salts such as alkali metal sesquicarbonates (for example trona) which comprise bicarbonate. Sodium or potassium bicarbonates or trona are especially suitable. Bicarbonates in the strict sense are recommended. Potassium bicarbonate or sodium bicarbonate, more particularly sodium bicarbonate, are preferred. Regarding the silica, it is recommended that this is in amorphous form, and not crystalline form, for the tolerance thereof by the human body.

In the present invention, the silica may for example be silica in the strict sense such as fumed silica or precipitated silica. However, in this document, it also covers minerals comprising at least 30%, advantageously at least 50% by weight of silica. Among these minerals mention may be made of: phonolite, fuller's earth, diatomaceous earths, potassium feldspars such as orthoclase ($KAlSi_3O_8$), calcium-sodium feldspars such as albite ($NaAlSi_3O_8$) and anorthite ($CaAl_2Si_2O_8$). Phonolite, fumed silica or precipitated silica are especially suitable. Fumed silica or precipitated silica are preferred.

It is preferred for the silica to be in the form of very fine particles, having a high specific surface area. According to the present invention, the specific surface area of the silica is in general at least 5 $m^2/g$, advantageously at least 50 $m^2/g$, preferably at least 100 $m^2/g$, most preferably at least 200 $m^2/g$. The specific surface area is measured according to the standard ISO 5794-1, annex D. In one advantageous embodiment of the invention, the silica consists of silica grains having a weight-average diameter at most equal to 20 µm, advantageously at most equal to 15 µm.

The alkali metal bicarbonate of the composition milled in the presence of silica advantageously consists of bicarbonate grains having a weight-average diameter before milling of at least: 100 µm, or 130 µm, or 170 µm, or 210 µm.

The term "milling" is understood in the present invention to mean a physical operation that enables the reduction of solid granules to fragmented particles that are smaller and are such that the weight-average diameter of said fragmented particles is at least 10% smaller with respect to the weight-average diameter of the granules before milling. In one preferred embodiment of the invention, the milling of the bicarbonate grains is such that the weight-average diameter of the particles obtained by milling have a weight-average diameter that is advantageously at least 30%, more advantageously at least 50%, preferably at least 75%, more preferably at least 90%, most preferably at least 95% smaller with respect to the weight-average diameter of the grains before milling.

The milling may be carried out by any physical means known to a person skilled in the art. The physical means include mechanical or pneumatic means, such as impact, crushing, autogenous crushing, spraying, shock wave and ultrasound milling systems. The milling systems comprising an impact mill are advantageous. Among these systems, those comprising an impact mill selected from hammer mills, plate rotor/stator mills and pin rotor/stator mills are particularly suitable. The milling systems comprising an impact mill selected from plate rotor/stator mills and pin rotor/stator mills are preferred.

Among the milling systems comprising an impact mill, those provided with a particle size selector that enables a recycling of the particles of large particle size are particularly advantageous.

In a first variant of the present invention, besides the alkali metal bicarbonate and the silica, the remainder of the composition may contain other mineral salts or organic compounds known for their parasiticidal properties. In a second variant of the present invention, the parasiticidal composition is free of any neurotoxic active principle. In a third variant of the present invention, the parasiticidal composition is free of any other organic parasiticidal active principles. In a fourth variant of the present invention, the parasiticidal composition is even free of any other parasiticidal active principles. Among the parasiticidal compositions of this fourth variant, the parasiticidal compositions consisting essentially or consisting of silica and of alkali metal bicarbonate are particularly advantageous. Among the alkali metal bicarbonates, sodium bicarbonate has a good cost/effectiveness relationship, thus, among these parasiticidal compositions, those consisting essentially or consisting of silica and of sodium bicarbonate are very particularly advantageous.

The invention also relates to a parasiticidal composition capable of being obtained by this method and the use of the composition. Indeed, it has been observed that a mixture of milled alkali metal bicarbonate and of silica produced in a conventional powder mixer, such as blade mixers equipped with lifter blades, have many silica agglomerates of greater than 1000 µm. These agglomerates are however friable with a small pressure by the fingers of one hand.

On the other hand, and in a particularly advantageous embodiment, the parasiticidal composition of the present invention, having greatly increased effectiveness, is free of silica agglomerates of greater than 1000 µm. Indeed, after milling the silica agglomerates that can be observed using an optical microscope are rarely greater than 300 µm in the present invention.

The invention also relates to the use of the parasiticidal composition in powder form or in the form of a suspension in a liquid.

The parasiticidal compositions thus manufactured are especially effective against mites. They are also effective against lice, ticks, bugs, weevils and lesser mealworm.

Moreover, the parasiticidal compositions are also effective against fungi. Thus, the invention also relates to the use of the parasiticidal compositions, obtained by the manufacturing method according to the present invention, for its combined parasiticidal and antifungal effects. These compositions are particularly harmless to humans and animals, and have a wide application range.

The parasiticidal compositions manufactured according to the present invention may be used in powder form. They may be applied by any appropriate known means such as dusting, spraying, brushing, spraying, dispersion by an aeration device or mixing. They may advantageously be used in the form of powder applied by dusting and/or applied by an aeration device. One of the modes of use in the form of powder applied by an aeration device is described in particular in patent application FR1154773 (SOLVAY S.A.).

They may thus be used in the treatment of the human environment. The term "environment" is understood to mean all the surfaces on which the parasites may be caused to alight, move or develop. The human environment includes, for example, the walls and door or window frames of dwellings, floors, rugs or carpets, fitted carpets, armchairs, bedding, mattresses, pillows, cushions, draperies, textiles for clothes, soft toys and various fleeces. Among the parasites particularly sensitive to such powders mention may be made of mites, in particular dust mites, which are responsible for various types of allergy. Among the dust mites, mention may especially be made of *Dermatophagoides pteronyssinus*. Among the parasites particularly sensitive to such powders mention may also be made of bugs, more particularly bed bugs such as *Cimex lectularius*.

The amounts of powders to be used are generally at least 5 g/m$^2$, advantageously at least 10 g/m$^2$, more advantageously at least 20 g/m$^2$. It is generally of no benefit to apply more than 60 g/m$^2$.

The parasiticidal compositions manufactured according to the method of the present invention may also be used in the treatment of the animal environment, in particular the environment of pets and livestock animals. The animal environment includes, for example, livestock buildings, bedding, cages, nest boxes and nests. It is then recommended to use amounts equivalent to those mentioned for the treatment of the human environment indicated above.

The parasiticidal compositions manufactured according to the method of the present invention may also be used in the treatment of construction materials. In particular, the treatment of construction materials comprising natural fibres or wood. The expression "natural fibre" is understood to mean a fibre of plant origin such as flax, flax shives, hemp, stalk of peeled hemp, jute, sisal, coir, cotton, and wood, or of animal origin such as wool, and feather. The natural fibre may be virgin (first use) or recycled such as for example cotton (used clothing), or cellulose (old papers, boards). The powder manufactured according to the present invention is then incorporated preferably uniformly in the mass where it is desired to control the development of parasites, or the development of parasites and fungi. The amounts used are in general at least 1% by weight, advantageously at least 5%. In general it is not very beneficial to apply more than 20% by weight relative to the total weight of material.

The parasiticidal compositions manufactured according to the method of the present invention may also be used in the treatment of cereal plants, especially in view of the storage thereof and transport thereof. They exhibit, in particular, an increased effectiveness against certain parasites. Among these parasites, mention may be made of wheat mites such as *Acarius Siro* and *Tyrophagus putrescentiae*, wheat weevils such as *Sitophilus granarius*, grain borers such as *Rhyzopertha dominica*, and grain beetles such as *Oryzaephilus surinamensis*. The compositions moreover remain active against cereal plant moulds such as *Aspergillus* and *Penicillium*. When the cereal plants are intended for human or animal food, food-grade alkali metal bicarbonates and silica are used.

The present invention also relates to the use of such parasiticidal compositions in the form of a suspension. In the present document, the term "suspension" is understood to mean a suspension of the parasiticidal composition manufactured according to the method of the present invention in a liquid, advantageously a solvent of the alkali metal bicarbonate. The solvent may be selected from water, organic liquids, natural oils, synthetic oils, and mixtures thereof. The liquid is advantageously selected from water and oils.

Water is advantageous for the following type of uses: treatment of the human environment, treatment of the animal environment, treatment of cereal plants before storage, treatment of construction materials during their manufacturing phase or during the installation thereof. In one advantageous mode of the present invention, water is used with parasiticidal compositions manufactured according to the method of the present invention, at concentrations such that the solubility limit of the alkali metal bicarbonate in water is attained. In this case, when the parasiticidal composition is applied in the form of an aqueous suspension, a film of undissolved alkali metal bicarbonate grains and silica grains bonded by a thin layer of dried alkali metal bicarbonate is formed. Such a layer has the advantage of remaining active against parasites, and of not being gelatinous after drying. In a first particularly advantageous mode of this advantageous mode, the suspension is of the type of that described in European patent EP 0 352 847 (SOLVAY S.A.). In a second particularly advantageous mode of this advantageous mode, the suspension is of the type of that described in application WO 2006/097480 (SOLVAY S.A.).

This advantageous mode is recommended in the case of use in the treatment of vertical walls or complex surfaces of the human or animal environment. Among the complex surfaces of the animal environment, mention may be made, for example, of cages or nest boxes. This advantageous mode is also recommended in the treatment of cereal plants. Specifically, in this case, all or some of the parasiticidal composition adheres to the cereal plants; which limits the segregation, after drying, of the suspension, of the parasiticidal powder and of the cereal plants treated during the handling thereof and the transport thereof. In a third particularly advantageous mode of this advantageous mode, the suspension is in the form of a gel, in particular in the form of an aqueous gel of the type of that described in application WO 2007/04608 (SOLVAY S.A.).

Oil, in particular natural oils, such as linseed oil, is advantageous for uses of the type for treating construction materials made of natural fibres such as flax or hemp. Fibres of this type exhibit a good absorption of these oils and make it possible to fix all or some of the parasiticidal composition to the fibres. This generally avoids a step of drying the construction material.

The dispersion of the parasiticidal composition in the liquid may be carried out by any means known to a person skilled in the art. Mixers equipped with pitched blade agitators, or with shearing turbine agitators such as Rushton turbine agitators or the like, and paint mixers are in general suitable. Turbine agitators for paints are recommended when the densities of suspensions of alkali metal bicarbonate and of silica in the liquid are greater than 20% by weight relative to the total weight of the suspension.

The parasiticidal compositions thus manufactured are especially effective against mites. They are also effective against lice, ticks, moths, weevils and lesser mealworm.

Moreover, the parasiticidal compositions are also effective against fungi. Thus, the invention also relates to the use of the parasiticidal compositions, obtained by the manufacturing method according to the present invention, for its combined parasiticidal and antifungal effects. These compositions are particularly harmless to humans and animals, and have a wide application range.

Thus, the present invention also relates to the use of the parasiticidal composition obtained by the method of the present invention and used in the form of a suspension in a liquid or in the form of a gel.

The present invention also relates to the use of the parasiticidal composition used in the form of powder, in particular in the form of a powder applied by dusting and/or applied by an aeration device, or in the form of a suspension in a liquid or in the form of a gel, for protecting cereal plants.

The present invention also relates to the use of the parasiticidal composition used in the form of powder, in particular in the form of a powder applied by dusting and/or applied by an aeration device, or in the form of a suspension in a liquid or in the form of a gel, for controlling the development of parasites in the animal environment, in particular in the environment of livestock animals.

The following examples serve to illustrate the invention. They are not limiting.

Examples 1 and 2

In this series of examples, tests were carried out on mites by comparing the effectiveness of the parasiticidal compositions produced according to:

the prior art method (mode 1 not in accordance with the invention): mixing of fine components, alkali metal bicarbonate and silica, and the method of the present invention (mode 2 in accordance with the invention): simultaneous milling of alkali metal bicarbonates and silica.

For this purpose, use was made of 0 to 500 µm sieved SOLVAY Bicar® Z animal food grade sodium bicarbonate, having a particle size distribution characterized by a weight-average diameter D50=210 µm and a span (D90-D10)/D50=1.20 (D90=350 µm and D10=95 µm).

Produced for these comparative tests were compositions consisting of sodium bicarbonate, at a content of 85% by weight, and of Sipernat 50 silica (Degussa/Evonik), at a content of 15% by weight according to the prior art method (mode 1) and the method of the present invention (mode 2).

For each test according to the mode in accordance with the invention (mode 2) the sodium bicarbonate and the silica were co-milled (mode 2 in accordance with the invention) so as to obtain a parasiticidal composition having a particle size distribution such that at least 50% by weight of the particles have a diameter of less than 100 µm, advantageously of less than 30 µm. To do this, 0.85 kg of sodium bicarbonate and 0.15 kg of the silica corresponding to each type of test were pre-mixed in a stainless steel Lödige mixer with lifter blades and having a working volume of 3 liters in order to obtain the mixture in the desired proportion. The bicarbonate and silica of this mixture were then co-milled in a Hosokawa-Alpine UPZ100 mill rotating at 17 600 rpm, equipped with a stainless steel pin rotor/stator system feeding the mixture into the mill at a rate of 1.5 kg/h.

So as not to introduce bias into the comparative tests (mode 1 according to the prior art and mode 2 according to the present invention) relating to the respective particle sizes of the alkali metal bicarbonate and of the silica, the following were carried out: the particle size distribution of the mixture obtained in accordance with the present invention (mode 2) was measured, and then the particle size distribution of only the silica of the composition obtained was measured (still mode 2). In order to measure the particle size distribution of only the silica of the composition, the silica being highly insoluble compared to the bicarbonate, the alkali metal bicarbonate of the composition was dissolved in an excess of water, then the silica was filtered on a Büchner flask and filter paper, the silica was washed with water and then with ethanol.

In order to carry out the comparative test with mode 1 (not in accordance with the invention) the sodium bicarbonate and the silica were then milled separately, adjusting the speed of the rotor and the feed throughput of each powder so as to obtain the same D50 values (to within 5%) for each of the powders (bicarbonate and silica) as those measured in mode 2 (in accordance with the invention) described above. Next, the two milled constituents were mixed in the Lödige mixer with lifter blades in order to obtain a parasiticidal composition according to mode 1. Examples of various particle sizes obtained are given in Table 1.

Each parasiticidal composition according to each of the 2 modes was evaluated on red mites according to the following procedure. The mites used (*Dermanyssus gallinae*) originate from the industrial breeding of poultry (SOGEVAL origin). The sensitivity of the strain to the main families of insecticides was verified. Around 200 mites of all stages were placed on 15 cm-side galvanized sheet metal plates that had been pretreated with the various compositions. A Petri dish lid covers the plates on a rubber seal in order to prevent escapes. The composition is dispersed in water to a concentration of 50% by weight. The suspension obtained is sprayed over the sheet metal plates. The amount of suspension applied corresponds approximately to 17 g of alkali metal bicarbonate per square meter of surface treated, and 20 g of parasiticidal composition in total per square meter of surface treated. The mortality of the mites was noted after 1, 2, 3, 4, 5, 6 and 24 hours. A control batch was monitored at the same time in order to know the natural mortality of mites subjected to the same conditions. Three repetitions were carried out for the experimental series and the average of the three values was taken. The experimental mortality test conditions were: temperature 22° C.±1° C.; 70%±5% relative humidity; lighting 1500 lux.

The comparative result of the mortality rates of the mites obtained with each of the compositions is given in Table 2. Monitoring on an untreated control plate gives 0% mortality over the first 6 hours. The repeatability of the mortality rates on red mites is ±3% when mortality is measured. After 2 hours of exposure, a mortality rate of 46% is observed for Example 1 (in accordance with the invention) versus 36% for the composition according to Example 2 (not in accordance with the invention).

TABLE 1

Comparative particle sizes of the powders of modes 1 & 2

| Examples | Powder | Mode | D90 μm | D50 μm | D10 μm | Span |
|---|---|---|---|---|---|---|
| — | Solvay Bicar Z | as is | 350 | 210 | 95 | 1.2 |
| — | Sipernat 50S silica | as is | 33 | 17.3 | 7 | 1.5 |
| 1 | Composition | mode 2 | 28 | 11.9 | 3 | 2.1 |
| 1 | Insoluble material (silica) of the composition | mode 2 | 23 | 13.9 | 8 | 1.1 |
| 2 | UPZ milled Solvay Bicar Z | mode 1 | 27 | 11.3 | 3 | 2.2 |
| 2 | UPZ milled Sipernat 50S silica | mode 1 | 26 | 13.8 | 7 | 1.3 |

TABLE 2

*Dermanyssus gallinae* mortality rate - Examples 1 and 2

| Example | Ref. Test | 1 h | 2 h | 3 h |
|---|---|---|---|---|
| 1 (in accordance) (mode 2) | E27b 85% Bicar Z, 15% Sipernat 50S silica, UPZ co-milled | 5% | 46% | 100% |
| 2 (not in accordance) (mode 1) | E27b 85% milled Bicar Z, 15% milled Sipernat 50S silica, mixed | 4% | 36% | 100% |

Examples 3 to 9

In this series of examples, the same procedure as in Examples 1 and 2 was followed, but the Sipernat 50 silica was replaced in the compositions by:

Tixosil 331 silica (Rhodia) in Examples 3 and 4,
Tixosil 38AB silica (Rhodia) in Examples 5 and 6,
Sylysia 370 silica (Sylisiamont) in Examples 7 and 8, or
Vulkanit 500 phonolite (Hauri) comprising 36 to 42% of $SiO_2$, having a D92<35 μm in Example 9.

The mortality rate on *Dermanyssus gallinae* mites (red mites) is given in Table 3. A higher parasite mortality at 3 hours is observed with the method according to the present invention (mode 2) in Examples 3, 5 and 7 than with the known prior art method (mode 1) respectively in Examples 4, 6 and 8. Example 9 in accordance with the present invention (mode 2) carried out with phonolite also shows excellent results at 3 hours.

Examples 10 to 15

In this series of examples, the natures of the alkali metal bicarbonates are varied. Parasiticidal compositions are produced that are tested on *Dermanyssus gallinae* mites according to Examples 1 and 2, but the sodium bicarbonate is replaced by ammonium bicarbonate $NH_4HCO_3$ (Examples 10 and 13), by sodium sesquicarbonate $Na_2CO_3.NaHCO_3.2H_2O$ (Examples 11 and 14), or by potassium bicarbonate $KHCO_3$ (Examples 12 and 15). The particle sizes of the selected alkali metal bicarbonates are close to that of the sodium bicarbonate used in Examples 1 and 2.

The mortality rate of *Dermanyssus Gallinae* after 2 and 8 hours of exposure with the compositions manufactured according to the prior art (mode 1) are respectively:

21% and 100% (Example 10—Ref. test E20)
38% and 100% (Example 11—Ref. test E20)
47% and 100% (Example 12—Ref. test E20)

A control treated with water gives a mortality rate of 0% after 2 and 8 hours of exposure.

The effectiveness of the compositions manufactured according to the present invention (mode 2) on *Dermanyssus gallinae* measured by the mortality rate at 1, 2, 4 and 24 hours (Examples 13, 14 and 15) are systematically superior to that of the compositions manufactured according to the prior art (mode 1).

Examples 16 to 17

In this series of examples, two parasiticidal compositions were prepared in the same way as that described in Examples 1 and 2. These two parasiticidal compositions were tested on insects instead of mites. The insects selected were selected for their good representativeness of crawling insects.

Examples 16 and 17 were carried out with *Sitophilus granarius* (grain weevils).

The effectiveness of the compositions prepared was evaluated according to the following procedure: 1000 ppm, i.e. 1 g of parasiticidal composition per kg of wheat were incorporated into 2 kg batches of wheat seeds (wheat free of insecticide residues, originating from organic farming) using a laboratory mixer (rotating inclined drum). Deposited into these treated batches were 25 adult insects of both sexes aged from 2 to 4 weeks old, originating from an official French strain (INRA Bordeaux). Three repetitions were carried out, including without product for one series, for which the insects undergo the same handling operations (to verify the harmlessness of the grains and the viability of the living material). The mortality of the insects is noted.

The effectiveness of the composition (in accordance with the invention) produced in Example 1 was tested twice (Examples 16 and 16') in order to examine the repeatability thereof. The effectiveness of the composition produced according to Example 2 (not in accordance with the invention) was tested once (Example 17).

The mortality results of the grain weevils at 3, 7, 10, 14, 21, 30 and 42 days are given in Tables 4 and 5. These tables clearly show the increase in effectiveness of the parasiticidal composition according to the present invention (Examples 16 and 16'): with 100% insect mortality from 24 hours and at least up to 42 days, whereas the composition that is not in accordance (Example 17) prepared according to the prior art shows a zero mortality rate of the weevil at 24 hours and that is limited to 81% at 42 days.

Example 18

In this example, tests are carried out on strains of fungi cited as pathogens in the breeding of animals such as poultry or cattle, in order to evaluate the fungicidal effectiveness of the parasiticidal composition manufactured according to the present invention.

For this purpose, 1.5 kg of Tixosil 38AB amorphous silica (Rhodia) are mixed with 3.5 kg of Bicar Z 0/50 sodium bicarbonate (Solvay), the particles of which have a particle size distribution such that 50% by weight have a diameter of less than 220 μm, in a Lödige pedestal mixer for 5 minutes. The sodium bicarbonate and silica mixture is then milled in a Hozokawa Alpinea UPZ 100 mill at 8000 rpm in order to obtain a powder such that 75% of the particles have a diameter of less than 65 μm.

The powder thus obtained is then mixed with 5 kg of Bicar 0/4 (Solvay), the particles of which have a particle size distribution such that 50% by weight have a diameter of less than 20 μm, in the same pedestal mixer for 5 minutes.

The powder thus obtained is deposited directly on an agar medium seeded with *Penicillium expansum, Aspergillus candidus, Aspergillus ochraceus, Aspergillus glaucus* group, *Penicillium* sp and *Scopulariopsis*. The areas of inhibition, that is to say the areas where the growth of the fungus is stopped by the action of the powder, are very pronounced.

Should the disclosure of any patent, patent applications, and publications that are incorporated herein by reference conflict with the present description to the extent that it might render a term unclear, the present description shall take precedence.

TABLE 3

*Dermanyssus gallinae* mortality rate - Examples 3 to 9

| Examples | Ref. | Study and Type of Tests | Exposure time | | | | | | |
|---|---|---|---|---|---|---|---|---|---|
| | | | 1 h | 2 h | 3 h | 4 h | 5 h | 6 h | 24 h |
| 3 (in accordance) | E12 | 85% Bicar Z + 15% Tixosil 331 silica, UPZ milled | 0.5% | 32% | 100% | 100% | 100% | 100% | 100% |
| 4 (not in accordance) | E12 | 85% milled Bicar Z + 15% Tixosil 331 silica, mixed | 0% | 8% | 17% | 41% | 72% | 91% | 100% |
| 5 (in accordance) | E48 | 85% Bicar Z + 15% Tixosil 38AB silica, UPZ milled | 0.5% | 28% | 100% | 100% | 100% | 100% | 100% |
| 6 (not in accordance) | E48 | 85% milled Bicar Z + 15% Tixosil 38AB silica, mixed | 0% | 0% | 5% | 13% | 48% | 100% | 100% |
| 7 (in accordance) | E27b | 85% Bicar Z, 15% Sylysia 370 silica, UPZ milled | 6% | — | 99% | 100% | 100% | 100% | 100% |
| 8 (not in accordance) | E27b | 85% milled Bicar Z, 15% milled Sylysia 370 silica, mixed | 1% | — | 71% | 100% | 100% | 100% | 100% |
| 9 (in accordance) | E33a | 85% Bicar Z, 15% phonolite, UPZ milled | 2% | — | 62% | 100% | 100% | 100% | 100% |

TABLE 4

Mortality rate of *Sitophilus granarius* (wheat weevil) with composition in accordance with the invention - Examples 16 and 16'

| Example No. | | | Exposure time | | | | | | | |
|---|---|---|---|---|---|---|---|---|---|---|
| No. | Ref. | Type | 24 h | 48 h | 72 h | 96 h | 120 h | 144 h | 7 d | 14 d |
| 16 | E31A | Example 1 type composition at 1000 ppm | 100% | 100% | 100% | 100% | 100% | 100% | 100% | 100% |
| | E31A | Control | 0% | 0% | 0% | 0% | 0% | 0% | 3% | 3% |
| 16 | E31B | Example 1 type composition at 1000 ppm | 100% | 100% | 100% | 100% | 100% | 100% | 100% | 100% |
| | E31B | Control | 0% | 0% | 0% | 0% | 0% | 0% | 5% | 7% |

TABLE 5

Mortality rate of *Sitophilus granarius* (wheat weevil) with composition not in accordance with the invention - Example 17

| No. | Ref. | Type | 3 | 7 | 10 | 14 | 21 | 30 | 42 |
|---|---|---|---|---|---|---|---|---|---|
| 17 | E11 | Example 2 type composition at 1000 ppm | 0% | 17% | 24% | 44% | 55% | 68% | 81% |
|  | E11 | Control | 0% | 0% | 0% | 2% | 2% | 3% | 3% |

Columns 3–42 are Exposure time (days).

The invention claimed is:

1. A method for manufacturing a parasiticidal composition consisting essentially of:
   at least 40% by weight of alkali metal bicarbonate, and
   at least 1% of silica,
   said method comprising:
   milling at least 35% of the alkali metal bicarbonate of the composition in the presence of said silica in order to form a mixture of particles, and
   if necessary, adding the remainder of the alkali metal bicarbonate to said mixture of particles to form the parasiticidal composition,
   wherein said parasiticidal composition has a particle size distribution such that at least 50% by weight of the particles have a diameter of less than 100 μm.

2. The method according to claim 1, wherein the content of said alkali metal bicarbonate in the parasiticidal composition is at least 70% by weight.

3. The method according to claim 1, wherein the content of said silica in the parasiticidal composition is at least 5% by weight.

4. The method according to claim 1, wherein said milling is carried out with an alkali metal bicarbonate:silica weight ratio which is at most equal to: 100:1 and at least equal to 1:1.

5. The method according to claim 1, wherein at least 50% of said alkali metal bicarbonate of the composition is milled in the presence of said silica.

6. The method according to claim 1, wherein said milling is carried out with an alkali metal bicarbonate:silica weight ratio which is at most equal to: 100:1.

7. The method according to claim 6, wherein said alkali metal bicarbonate:silica weight ratio is at least equal to 1.

8. The method according to claim 1, wherein said silica has a specific surface area of at least 5 $m^2/g$.

9. The method according to claim 1, wherein said silica consists of silica grains having a weight-average diameter at most equal to 20 μm.

10. The method according to claim 1, wherein said alkali metal bicarbonate of the composition milled in the presence of said silica consists of bicarbonate grains before milling that have a weight-average diameter of at least 100 μm.

11. The method according to claim 1, wherein said alkali metal bicarbonate is sodium bicarbonate.

12. The method according to claim 1, wherein said milling of the at least 35% of the alkali metal bicarbonate of the composition milled in the presence of said silica is carried out with an impact mill.

13. The method according to claim 1, wherein said parasiticidal composition is used for protecting cereal plants or for controlling development of parasites in an environment of animals.

14. The method according to claim 13, wherein the parasiticidal composition in a powder form is used in an amount of at least 1% by weight relative to the total weight of said material.

15. The method according to claim 1, further comprising dispersing said parasiticidal composition in a liquid to form a suspension or a gel.

16. The method according to claim 15, wherein said liquid is a solvent of the alkali metal bicarbonate.

17. The method according to claim 1, wherein said parasiticidal composition is in form of a powder.

18. The method according to claim 1, wherein said parasiticidal composition is free of silica agglomerates of greater than 1000 μm.

* * * * *